United States Patent [19]

Hardy, Sr.

[11] 4,342,666
[45] Aug. 3, 1982

[54] ENHANCEMENT OF TRILITHIUM PHOSPHATE CATALYST ACTIVITY

[75] Inventor: Donald Hardy, Sr., Levittown, Pa.

[73] Assignee: FMC Corporation, Philadelphia, Pa.

[21] Appl. No.: 255,611

[22] Filed: Apr. 20, 1981

[51] Int. Cl.$^3$ ............................................. B01J 27/18
[52] U.S. Cl. ...................................... 252/437; 252/435
[58] Field of Search ......................... 252/413, 435, 437

[56] References Cited

U.S. PATENT DOCUMENTS

| | | | |
|---|---|---|---|
| 2,426,264 | 8/1947 | Fowler et al. | 568/908 |
| 2,945,822 | 7/1960 | Jacob | 252/413 X |
| 2,986,585 | 5/1961 | Denton | 252/435 X |
| 3,044,850 | 7/1962 | Denton | 423/313 |
| 3,067,256 | 12/1962 | Fischer et al. | 260/601 R |
| 3,090,815 | 5/1963 | Denton | 568/908 |
| 3,090,816 | 5/1963 | Denton | 568/908 |
| 3,092,668 | 6/1963 | Bruson et al. | 252/437 X |
| 3,122,588 | 2/1964 | Phillips et al. | 260/601 R |
| 3,238,264 | 3/1966 | Rowton | 568/908 |
| 3,255,258 | 6/1966 | Charles et al. | 568/908 |
| 3,274,121 | 9/1966 | Schneider | 252/437 |
| 3,325,245 | 6/1967 | Rowton | 252/437 X |
| 4,065,510 | 12/1977 | Schreyer et al. | 252/437 X |

*Primary Examiner*—W. J. Shine
*Attorney, Agent, or Firm*—Christopher Egolf

[57] ABSTRACT

A method for enhancing the activity of a trilithium phosphate catalyst, useful for isomerizing alkylene oxides to the corresponding alcohols, in which dry catalyst is contacted with an aqueous solution containing a mineral acid such as phosphoric acid, and the acid-treated catalyst is thereafter separated from the aqueous solution, preferably water-washed, and then dried. The amount of acid in the aqueous solution is adjusted so that the pH of the solution in contact with the catalyst is maintained at a value of between 9 to 11.

10 Claims, No Drawings

ENHANCEMENT OF TRILITHIUM PHOSPHATE CATALYST ACTIVITY

BACKGROUND OF THE INVENTION

1. Field of the Invention

This invention relates to trilithium phosphate isomerization catalysts and, more particularly, to a method of enhancing catalyst activity.

2. Background of the Prior Art

Trilithium phosphate ($Li_3PO_4$) is useful as a catalyst in the isomerization of alkylene oxides to their corresponding alcohols, particularly propylene oxide to yield allyl alcohol:

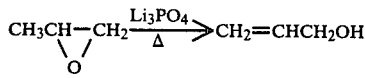

Several side reactions normally compete with the desired isomerization reaction, leading to the formation of compounds like propionaldehyde ($CH_3CH_2CHO$), 1-propanol ($CH_3CH_2CH_2OH$), and acrolein ($CH_2CHCHO$). It is desirable, of course, that the trilithium phosphate isomerization catalyst minimize formation of these byproducts.

The activity or efficiency of trilithium phosphate catalysts used for such purposes is ordinarily evaluated by its ability to convert a maximum amount of propylene oxide and to produce a high yield of allyl alcohol product with minimal byproducts. Conversion, a measure of the percentage of propylene oxide feed isomerized by the catalyst, is calculated thus:

$$\text{Conversion (\%)} = \frac{\text{propylene oxide reacted, wt.}}{\text{propylene oxide fed, wt.}} \times 100$$

Selectively, a measure of the purity of the allyl alcohol product that is expressed as a percentage, is calculated thus:

$$\text{Selectivity (\%)} = \frac{\text{allyl alcohol produced, wt.}}{\text{propylene oxide reacted, wt.}} \times 100$$

The amount of 1-propanol byproduct formed along with allyl alcohol is desirably minimized in the product. This is because separation of 1-propanol (B.P. 97.2° C.) from the allyl alcohol (B.P. 96.9° C.) by distillation is not easily accomplished due to their similar boiling points. The 1-propanol byproduct is expressed as a weight percentage of the allyl alcohol in the product, being calculated thus:

$$\text{1-propanol (\%)} = \frac{\text{1-propanol produced, wt.}}{\text{allyl alcohol produced, wt.}} \times 100$$

A satisfactory trilithium phosphate catalyst is generally one which has a conversion of at least 40%, a selectivity of at least 90% and which produces no more than 1% 1-propanol.

Various techniques are described in the patent literature for regenerating or reactivating trilithium phosphate catalysts. Activation/regeneration procedures applicable to trilithium phosphate catalysts are taught in U.S. Pat. Nos. 3,090,816 and 3,092,668, which involve treatment of the catalyst with various organic solvents at elevated temperature. U.S. Pat. No. 3,090,815 teachs an analogous treatment with water, at temperatures of from 50°–250° C. but notes that electrolyte-free water (e.g., distilled or demineralized water) is desirably used to avoid catalyst deterioration from the ion species.

These catalyst regeneration/activation techniques, however, have not been shown to improve trilithium phosphate catalyst efficiency such that 1-propanol byproduct formation is maintained below satisfactory levels.

SUMMARY OF THE INVENTION

In accordance with the present invention, the activity of trilithium phosphate isomerization catalysts is enhanced by the method which comprises contacting dry trilithium phosphate catalyst with an aqueous solution containing a mineral acid selected from the group consisting of $H_3PO_4$, HCl, $H_2SO_4$ and $HNO_3$, separating the acid-treated catalyst from the aqueous solution, and drying the activated catalyst, wherein the amount of acid in the aqueous solution is adjusted so as to maintain the pH of the solution in equilibrated contact with the catalyst at a value of between 9 to 11.

Phosphoric acid is the preferred mineral acid, and the amount of acid is preferably adjusted so as to maintain the pH of the solution in contact with the catalyst at a value of from 9.5 to 10.5.

The acid-treated catalyst, after its separation from the aqueous solution, is preferably water-washed.

DETAILED DESCRIPTION

The pH treatment of this invention involves contacting dry trilithium phosphate catalyst with an aqueous solution containing a mineral acid. An objective of the pH treatment is to maintain the alkalinity of the aqueous solution is essentially equilibrated contact with the catalyst at a pH value of from 9 to 11. Preferably the pH of the aqueous solution is maintained at a value of from 9.5 to 10.5, most preferably at about 10.

Enhanced catalytic activity is achieved when the catalyst being treated by the method of this invention is substantially dry and is not moist or water-wet.

The pH adjustment is achieved through use of an aqueous solution which contains a mineral acid, which may be phosphoric ($H_3PO_4$), hydrochloric (HCl), sulfuric ($H_2SO_4$) or nitric ($HNO_3$) acid. Phosphoric acid is the preferred mineral acid.

The strength of the acid employed for adjusting the pH is not critical and may range from very dilute to very concentrated. Dilute to moderately concentrated acid strengths (5–30 wt%) are preferred to avoid localized excessive concentrations of acid during the pH adjustment.

The pH treatment of the catalyst may employ an aqueous solution, e.g., water, to which the acid is added as necessary to achieve the desired pH or may utilize an aqueous solution of the mineral acid. In the latter situation, the proper pH may be achieved by varying the relative amounts of catalyst and aqueous solution or by introducing additional acid as necessary to the aqueous acid solution in contact with the catalyst.

The contact time duration between the aqueous acid solution and solid catalyst is not critical and may be as short as a few seconds or as long as several hours. The contact time should be sufficient in duration to achieve equilibration between the pH-adjusted aqueous solution and catalyst and ordinarily need be no more than a few (1–30) minutes.

In one embodiment of the invention, the dry catalyst is slurried in the aqueous solution and sufficient mineral acid added to adjust the alkalinity of the equilibrated aqueous mixture to the desired pH value. The catalyst slurry may have a concentration of from 1-40 wt% solids but preferably has a concentration of from 5-10 wt% solids. The aqueous slurry is preferably agitated so as to ensure good contact of the catalyst and aqueous solution and achieve equilibration between the two in a short time.

Temperature of the aqueous solution likewise is not critical and may vary from about 0° C. to 100° C. but is preferably at about ambient to 60° C., more preferably from 10° to 60° C.

After the pH treatment with the aqueous acid solution, the solid catalyst is separated from the aqueous solution by conventional means such as filtration, centrifugation, decanting, and the like.

The acid-treated catalyst is then preferably washed with water, sufficient water being utilized in either single or multiple washes to remove traces of the aqueous acid solution from the catalyst. Minimal water washing is desirable since excessive water washing may leach residual alkaline values from the catalyst and result in deterioration of catalyst activity. Temperature of the water wash may range from 0° to 100° C., with ambient to 60° being preferred.

Catalyst Evaluation Procedure

The trilithium phosphate catalysts were evaluated for catalytic performance in isomerizing propylene oxide to allyl alcohol using the following standardized procedure, to permit comparison of the various catalysts studied.

The laboratory scale isomerization reactor consisted of a cylindrical glass tube (45 mm diameter, 350 mm length) fitted with a medium porosity fritted glass disc at the bottom. The glass reactor was fitted with a thermowell and was wrapped with resistance heating tape to control temperature within ±1° C.

The reactor was charged with 80.0 g trilithium phosphate catalyst contained in 350 g of Therminol ® 66, a modified terphenyl heating fluid available from Monsanto Company. Gaseous propylene oxide was introduced into the bottom of the reactor at a constant rate (170-172 gm/hr), having been preheated to a temperature of about 270° C. The reactor was maintained at a temperature of 275° C.

After equilibration, the reactor was operated at steady state during the test which lasted for one hour. Precise mass balance measurements were made during the test, and the crude overhead product leaving the reactor was collected for analysis by gas liquid chromatography (g.l.c.).

The g.l.c. data were then utilized to calculate conversion, selectivity (yield), and 1-propanol formation for the catalyst tested.

EXAMPLE 1

Commercially available trilithium phosphate catalyst, obtained from Daicel Limited, Tokyo, Japan, was evaluated for its efficiency in producing allyl alcohol from propylene oxide. Conversion and selectivity of the catalyst were found to be satisfactory, at 52.6% and 93.6%, respectively. Formation of 1-propanol byproduct was deemed unsatisfactory at 1.53%.

In the pH treatment according to this invention, 90 g of the Daicel catalyst were slurried in 1.4 l of water, at a temperature of 25° C., in a 2 l beaker which was provided with a means for stirring. The pH of the slurry, determined as being 11.4, was then adjusted by the slow addition over a two minute period of phosphoric acid solution (20% $H_3PO_4$), with stirring, until the pH had decreased to about 10.0.

The catalyst was next separated from the solution by vacuum filtration, washed with 500 ml distilled water at a temperature of 50° C., and dried at a temperature of 140° C.

When the treated catalyst was evaluated for its catalytic activity, conversion and selectivity were virtually unchanged, (52.4% and 93.7% respectively) but formation of 1-propanol had decreased significantly to a satisfactory level, 0.96% from the previous unacceptable 1.53%.

COMPARATIVE EXAMPLE A

Trilithium phosphate catalyst was prepared from the reaction of lithium hydroxide and trisodium phosphate solutions by the following procedure.

Trisodium phosphate solution was prepared in a nitrogen-purged 5 l flask, into which was first charged 1050 ml distilled water and 264.5 g 97.0% sodium hydroxide pellets (6.42 g-moles). From an addition funnel containing 1632 g 12.22% $H_3PO_4$ solution (2.03 g-moles), phosphoric acid was then introduced over a 15-20 minute period into the stirred sodium hyroxide solution at a temperature maintained below 60° C.

Lithium hydroxide was prepared in a 5 l flask, into which was charged 1800 ml distilled water, 239 g LiOH.$H_2O$ (5.69 g-moles) and 69 g sodium hydroxide pellets (1.67 g-moles). The resultant lithium hydroxide/sodium hydroxide solution was heated to a temperature of 50° C., with stirring.

The entire trisodium phosphate solution prepared as described above, at a temperature of 50° C., was then added rapidly to the stirred LiOH/NaOH solution, the addition requiring only 24 seconds.

The resultant slurry of trilithium phosphate catalyst was maintained at a temperature of 40°-50° C., with stirring, for 4.5 minutes, after which stirring speed was reduced from 1200 rpm to 400 rpm and continued for another 25 minutes. The stirring was halted and the mixture allowed to sit at a temperature of 42°-43° C. before the solid catalyst was filtered under vacuum from the solution through a fritted glass filter.

The filtered trilithium phosphate catalyst solids were then washed five times, using 1500 ml distilled water at a temperature of 50°-60° C. for each wash. In each washing, the solids were reslurried in the water and stirred for five minutes before being vacuum filtered.

The trilithium phosphate catalyst was then dried in an oven for about 18 hours at a temperature of 140° C. and evaluated for its catalytic efficiency with the following results: conversion, 46.4%, selectively, 95.4%, and 1-propanol formation, 1.27%. The 1-propanol formation, being nearly 1.3%, was deemed unsatisfactory.

EXAMPLES 2 to 5

In each of these Examples, a portion (86 g) of the dry trilithium phosphate catalyst was slurried with 1400 ml distilled water at ambient temperature in a beaker. The pH of the slurries was 11.4-11.5.

The pH of the slurry was then adjusted by the slow addition of phosphoric acid solution (25% $H_3PO_4$), with stirring, until the slurry pH has been decreased to the desired value. In Examples 2, 3, 4 and 5, the pH was acid-adjusted to final values of 11.0, 10.5, 10.0 and 9.0, respectively.

The pH-adjusted slurry in each Example was then filtered and the wet cake re-slurried with 500 ml water at a temperature of 40° C., with stirring for five minutes. The slurry was filtered, and the catalyst solids dried overnight at a temperature of 140° C.

The acid-treated catalysts in each of the Examples were evaluated for catalytic activity, i.e., conversion, selectivity and 1-propanol formation. Improved conversion and reduced 1-propanol formation were obtained for all Examples, with best results being achieved when the final pH values were adjusted to 10.0 to 10.5.

Results from Examples 2 to 5 are summarized in the table below. The table specifies catalyst activity, i.e, conversion, selectivity, 1-propanol formation, for each of the pH treatments. The table also includes trilithium phosphate from Comparative Example A which was subjected to the same procedure as described for Examples 2 to 5, except that there was no pH adjustment with acid.

|  | Example | | | | |
| --- | --- | --- | --- | --- | --- |
|  | A | 2 | 3 | 4 | 5 |
| Final pH Value | 11.4* | 11.0 | 10.5 | 10.0 | 9.0 |
| Conversion, % | 46.4 | 51.3 | 55.0 | 54.0 | 49.1 |
| Selectivity, % | 95.4 | 95.6 | 95.3 | 95.4 | 94.5 |
| 1-Propanol Formation, % | 1.27 | 1.12 | 1.18 | 1.03 | 1.0 |

*no acid treatment; pH of untreated catalyst slurry

I claim:

1. A method for enhancing the activity of a trilithium phosphate isomerization catalyst which comprises contacting dry trilithium phosphate catalyst with an aqueous solution containing a mineral acid selected from the group consisting of $H_3PO_4$, HCl, $H_2SO_4$ and $HNO_3$, separating the acid-treated catalyst from the aqueous solution and drying the activated catalyst, wherein the amount of acid in the aqueous solution is adjusted so as to maintain the pH of the solution in equilibrated contact with the catalyst at a value of from 9 to 11.

2. The method of claim 1 wherein the pH of the solution is maintained at a value of from 9.5 to 10.5.

3. The method of claim 1 wherein the temperature of the aqueous solution is maintained at from 10° to 60° C.

4. A method for enhancing the activity of a trilithium phosphate isomerization catalyst, which comprises slurrying dry trilithium phosphate catalyst in an aqueous solution, adjusting the alkalinity of the agitated, equilibrated aqueous slurry to a pH of from 9 to 11 with a mineral acid selected from the group consisting of $H_3PO_4$, HCl, $H_2SO_4$ and $HNO_3$, separating the catalyst from the aqueous solution, and drying the activated catalyst.

5. The method of claim 4 wherein the aqueous slurry of trilithium phosphate catalyst contains from 5 to 10 wt.% catalyst.

6. The method of claim 4 wherein the pH of the slurry is adjusted to about 9.5 to 10.5.

7. The method of claim 4 wherein the temperature of the aqueous slurry is maintained at from 10° to 60° C.

8. The method of claim 4 wherein the aqueous solution is a dilute phosphate acid solution.

9. The method of claim 1 or 4 wherein the mineral acid is phosphoric acid.

10. The method of claim 1 or 4 wherein the acid-treated catalyst is water washed following its separation from the aqueous solution.

* * * * *